US012569261B2

(12) United States Patent     (10) Patent No.:   US 12,569,261 B2

Seykora et al.     (45) Date of Patent:    Mar. 10, 2026

---

(54) BONE HARVESTING SYSTEM

(71) Applicant: Acumed LLC, Hillsboro, OR (US)

(72) Inventors: Andrew William Seykora, Portland, OR (US); Larry W. Ehmke, Portland, OR (US); Brent Lane Norris, Jenks, OK (US)

(73) Assignee: Acumed LLC, Hillsboro, OR (US)

( * ) Notice: Subject to any disclaimer, the term of this patent is extended or adjusted under 35 U.S.C. 154(b) by 193 days.

(21) Appl. No.: 18/240,454

(22) Filed: Aug. 31, 2023

(65) Prior Publication Data

US 2023/0404602 A1     Dec. 21, 2023

Related U.S. Application Data

(63) Continuation of application No. 17/314,620, filed on May 7, 2021, now Pat. No. 11,779,350, which is a (Continued)

(51) Int. Cl.
*A61B 17/16*     (2006.01)
*A61B 17/00*     (2006.01)
*A61B 17/32*     (2006.01)

(52) U.S. Cl.
CPC ...... *A61B 17/1635* (2013.01); *A61B 17/1615* (2013.01); *A61B 17/1633* (2013.01);
(Continued)

(58) Field of Classification Search
CPC ............ A61B 17/1635; A61B 17/1615; A61B 17/1633; A61B 17/164; A61B 2017/00862; A61B 2017/320064
See application file for complete search history.

(56) References Cited

U.S. PATENT DOCUMENTS

| | | | |
|---|---|---|---|
| 5,556,399 A | 9/1996 | Huebner | |
| 6,293,794 B1 | 9/2001 | McSpadden | |

(Continued)

FOREIGN PATENT DOCUMENTS

| | | | |
|---|---|---|---|
| CA | 2235483 A1 | 5/1997 | |
| JP | H11514905 A | 12/1999 | |

(Continued)

OTHER PUBLICATIONS

Second Office Action corresponding to related Japanese Patent Application No. 2021-517428 mailed Dec. 25, 2023, 4 pages.

(Continued)

*Primary Examiner* — Sameh R Boles

(74) *Attorney, Agent, or Firm* — Knobbe, Martens, Olson & Bear, LLP

(57) ABSTRACT

Bone harvesting system including methods and devices for obtaining and/or removing osseous debris from a bone using an auger having a flexible, helical fin projecting from a shaft. In an exemplary method, a leading end region of the auger is placed into a reamed portion of a bone's medullary cavity via an entry site extending into the bone. Osseous debris is driven toward the entry site with the auger. At least a portion of the osseous debris that has passed through the entry site is collected outside the bone. In some embodiments, the leading end region of the auger is deformed by contact between the helical fin and a wall of the medullary cavity, to conform the helical fin in the leading end region to a portion of the medullary cavity.

19 Claims, 8 Drawing Sheets

Related U.S. Application Data continuation of application No. 16/144,979, filed on Sep. 27, 2018, now Pat. No. 11,000,295.

(52) U.S. Cl.
CPC .. *A61B 17/164* (2013.01); *A61B 2017/00862* (2013.01); *A61B 2017/320064* (2013.01); *A61B 2217/005* (2013.01)

(56) References Cited

U.S. PATENT DOCUMENTS

| | | | |
|---|---|---|---|
| 6,719,803 B2 | 4/2004 | Bonutti | |
| 6,846,314 B2 | 1/2005 | Shapira | |
| 8,096,957 B2 | 1/2012 | Conquergood et al. | |
| 8,585,726 B2 | 11/2013 | Yoon et al. | |
| 9,381,031 B2 | 7/2016 | Rains et al. | |
| 2004/0191897 A1 | 9/2004 | Muschler | |
| 2005/0209530 A1 | 9/2005 | Pflueger | |
| 2009/0309024 A1 | 12/2009 | Steigerwald et al. | |
| 2012/0150190 A1 | 6/2012 | Rabiner et al. | |
| 2012/0172905 A1 | 7/2012 | Lee Shee et al. | |
| 2012/0172907 A1 | 7/2012 | Lee Shee et al. | |
| 2013/0103067 A1 | 4/2013 | Fabro et al. | |
| 2016/0287264 A1* | 10/2016 | Chegini | A61B 17/1644 |
| 2018/0242984 A1 | 8/2018 | Thommen et al. | |
| 2020/0100800 A1 | 4/2020 | Seykora et al. | |
| 2021/0259709 A1 | 8/2021 | Seykora et al. | |

FOREIGN PATENT DOCUMENTS

| | | | |
|---|---|---|---|
| JP | 2013500073 A | 1/2013 | |
| JP | 2018510026 A | 4/2018 | |
| WO | 2014041540 A1 | 3/2014 | |
| WO | 2016022529 A1 | 2/2016 | |

OTHER PUBLICATIONS

European Search Report from corresponding European Patent Application No. 19867310.5, mailed Mar. 12, 2024. 4 pages.

Japanese Office Action corresponding to related Japanese Patent Application No. 2021-517428 mailed Jun. 26, 2023, 9 pages.

Extended European Search Report corresponding to related European Patent Application No. 19867310.5 mailed Apr. 3, 2022, 6 pages.

Supplementary European Search Report corresponding to related European Patent Application No. 19867310.5 mailed Apr. 26, 2022, 4 pages.

Thomas, Shane, Authorized Officer, ISA/US, Commissioner for Patents, "International Search Report" in connection with related International Application No. PCT/US2019/052230, dated Dec. 5, 2019, 10 pages.

Thomas, Shane, Authorized Officer, ISA/US, Commissioner for Patents, "Written Opinion of the International Searching Authority" in connection with related International Application No. PCT/US2019/052230, dated Dec. 5, 2019, 8 pages.

Biomedical Enterprises, Inc., BoneHOG(TM) Surgical brochure, date unknown, 21 pages.

Carevature Medical, "Powered Decompression System for Use In The Entire Spine", Healthcare Professionals | Carevature Medical, (c) 2017, 8 pages.

Depuy Synthes, "Reamer/Irrigator/Aspirator (RIA)", Surgical Technique, (c) 2015, 36 pages.

Stryker, "Interventional Pain", Dekompressor for Clinicians, (c) 2004, 6 pages.

International Preliminary Report on Patentability corresponding to International Application No. PCT/US2019/052230; report dated Apr. 8, 2021; (10 pages).

* cited by examiner

BONE HARVESTING SYSTEM

PRIORITY CLAIM

The present application is a continuation of U.S. patent application Ser. No. 17/314,620 filed on May 7, 2021, which is a continuation of U.S. patent application Ser. No. 16/144, 979 filed on Sep. 27, 2018, now U.S. Pat. No. 11,000,295, which are each incorporated herein by reference in their entirety for all purposes.

MATERIAL INCORPORATED BY REFERENCE

The following application is incorporated herein by reference for all purposes: U.S. patent application Ser. No. 16/001,867, filed Jun. 6, 2018.

INTRODUCTION

An orthopedic reamer is a surgical tool to widen a cavity in a bone. The reamer may be utilized to cut the wall of a bone's medullary cavity, to prepare the bone to receive an intramedullary nail. The resulting osseous debris can have utility as a bone graft when transplanted to fill a bone void.

The Reamer/Irrigator/Aspirator (RIA) System, which is commercially available from DePuy Synthes, offers the ability to create and collect osseous debris with the same instrument. The RIA instrument simultaneously (1) reams a medullary cavity to create osseous debris, (2) irrigates the medullary cavity with fluid, and (3) aspirates the osseous debris in fluid from the medullary cavity. The aspirate is filtered to produce a paste that can be used as an autograft/ allograft having osteoconductive, osteoinductive, and osteogenic properties.

However, the RIA System has a number of disadvantages. The shaft of the RIA instrument is relatively stiff, which limits where the RIA instrument can enter the bone and still reach the medullary cavity. The stiffness also could cause the reamer of the RIA instrument to drift, resulting in non-uniform reaming (reaming off-center). Moreover, the cutting head of the RIA instrument requires formation of a relatively large entry site in the bone for introducing the cutting head into the medullary cavity, which could increase the risk of post-surgical complications. Furthermore, blood loss occurs since vacuum is being applied to the medullary cavity during reaming. The volume of blood loss depends on the amount of time vacuum is applied, which typically corresponds to the amount of time bone is being reamed. Finally, the RIA instrument can be complicated for the surgeon to operate because reaming, irrigation, and aspiration are occurring at the same time. New devices and methods are needed for harvesting bone.

SUMMARY

The present disclosure provides a bone harvesting system including methods and devices for obtaining and/or removing osseous debris from a bone using an auger having a flexible, helical fin projecting from a shaft. In an exemplary method, a leading end region of the auger is placed into a reamed portion of a bone's medullary cavity via an entry site extending into the bone. Osseous debris is driven toward the entry site with the auger. At least a portion of the osseous debris that has passed through the entry site is collected outside the bone. In some embodiments, the leading end region of the auger is deformed by contact between the helical fin and a wall of the medullary cavity, to conform the helical fin in the leading end region to a portion of the medullary cavity.

DETAILED DESCRIPTION

The present disclosure provides a bone harvesting system including methods and devices for obtaining and/or removing osseous debris from a bone using an auger having a flexible, helical fin projecting from a shaft. In an exemplary method, a leading end region of the auger is placed into a reamed portion of a bone's medullary cavity via an entry site extending into the bone. Osseous debris is driven toward the entry site with the auger. At least a portion of the osseous debris that has passed through the entry site is collected outside the bone. In some embodiments, the leading end region of the auger is deformed by contact between the helical fin and a wall of the medullary cavity, to conform the helical fin in the leading end region to a portion of the medullary cavity.

The methods and devices of the present disclosure may offer one or more of the following advantages. The leading end region of the auger may be introduced into the medullary cavity of a reamed bone via an entry site in the bone that is off-axis and/or smaller in diameter than the leading end region of the auger (in a relaxed configuration), offering the practitioner more options and resulting in less damage to the bone. Osseous debris may be collected more efficiently because the helical fin can wipe debris circumferentially from the wall of a medullary cavity, even when the cavity's diameter varies. The osseous debris may be formed with a reamer(s), which may be replaced with a non-cutting bone harvesting device that is dedicated to, and thus optimized for, removing the osseous debris from the bone.

Further aspects of the present disclosure are described in the following sections: (I) overview of bone harvesting devices, (II) methods of harvesting osseous debris, and (III) examples.

I. Overview of Bone Harvesting Devices

This section provides an overview of bone harvesting devices of the present disclosure, as illustrated by an exemplary bone harvesting device 50; see FIGS. 1-8.

Figure 1:
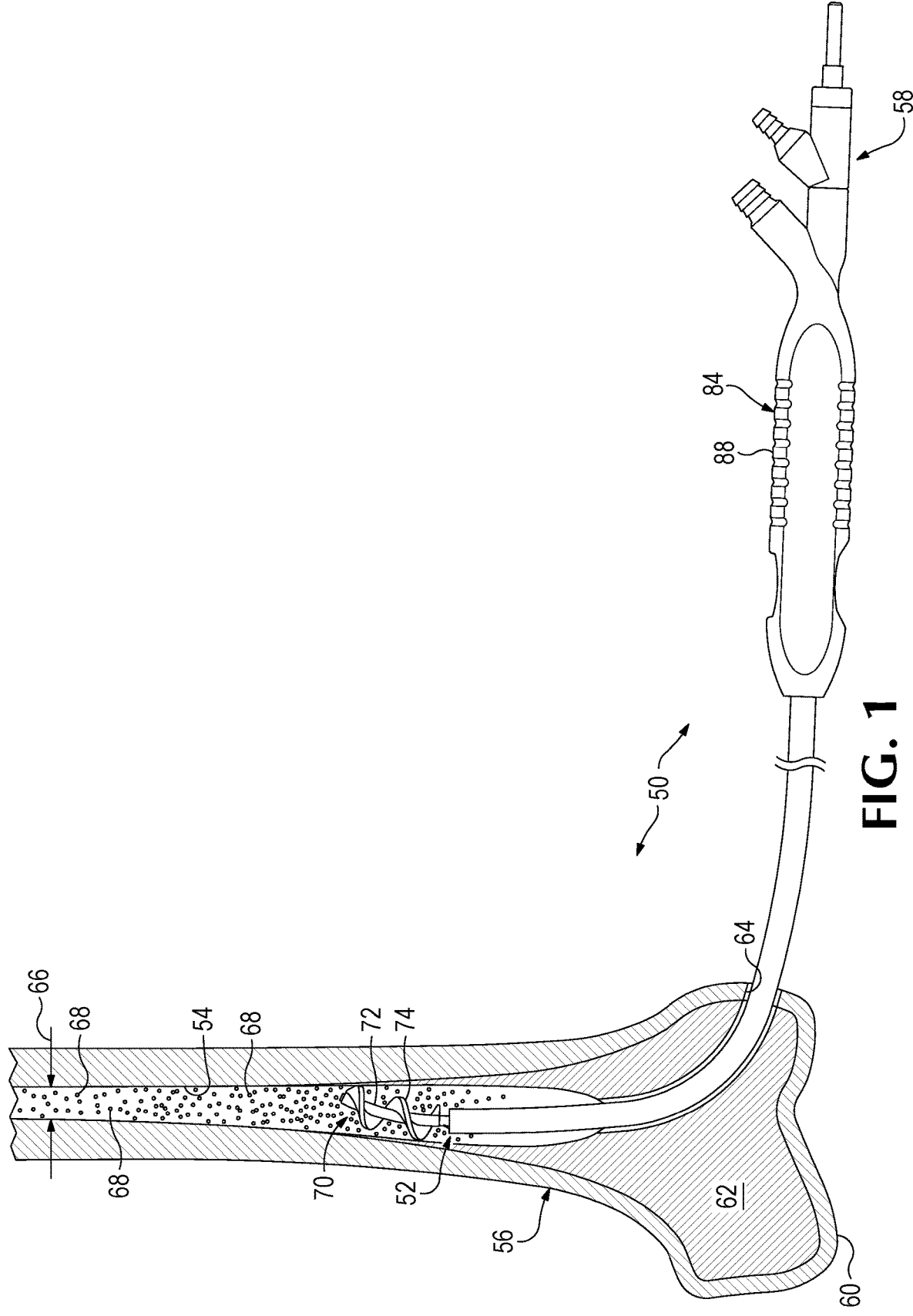
FIG. 1 is a view of an exemplary bone harvesting device extending into a reamed medullary cavity of a distal femur, which is shown sectioned, wherein the bone harvesting device includes a flexible auger to wipe the wall of the medullary cavity and propel bone debris axially.
Figure 2:
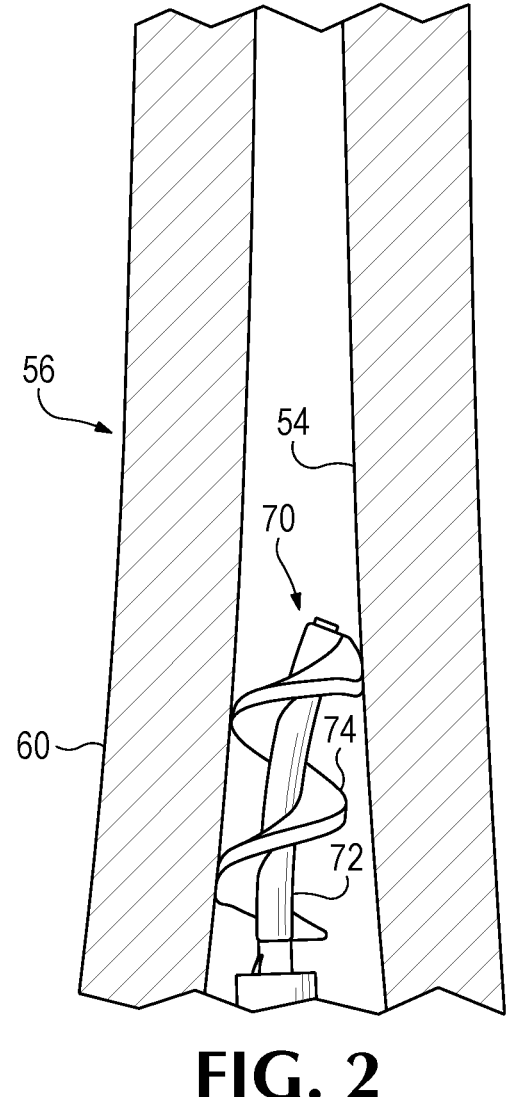
FIG. 2 is a fragmentary view of the bone harvesting device and femur of FIG. 1, taken with a leading end region of the auger located in a wider portion of the medullary and relatively less deformed by contact with the wall of the medullary cavity.
Figure 3:
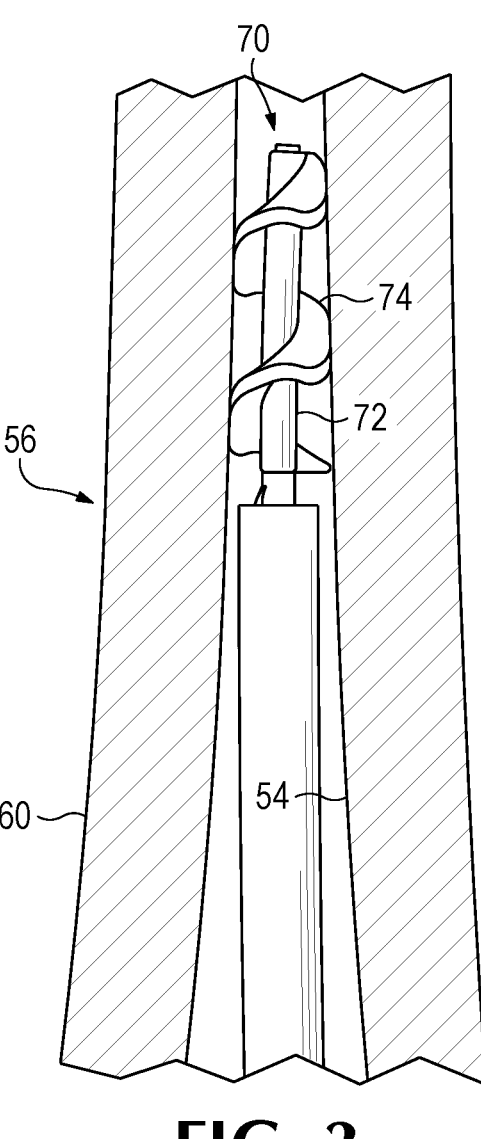
FIG. 3 is another fragmentary view of the bone harvesting device and femur of FIG. 1, taken with the leading end region of the auger located in a narrower, reamed portion of the medullary cavity and relatively more deformed by contact with the wall of the reamed portion of the medullary cavity.

FIG. 1 shows harvesting device 50 with a distal portion 52 located inside a medullary cavity 54 of a femur 56, and a proximal portion 58 remaining outside the femur. Cortical bone 60 forming a cortical shell of the femur, and cancellous bone 62 inside the cortical shell, are depicted. Distal portion 52 of harvesting device 50 has been inserted into femur 56 via an entry site 64 (an opening) formed in the exterior surface of the bone and extending into the bone. Before this insertion, medullary cavity 54 was reamed to a reamed diameter 66 with a reamer, which was advanced into the femur from entry site 64 and then removed. (Osseous debris includes osseous particles (morselized bone) and interchangeably may be called bone tissue or graftable bone.) Optionally, the reamer may utilize an expandable cutting head, which permits reamed diameter 66 to be larger than the diameter of entry site 64 and/or variable in size along the medullary cavity.

Harvesting device 50 includes an auger 70 (interchangeably called an auger conveyor) to move, or at least assist in moving, osseous debris 68 out of a reamed bone, such as femur 56, via entry site 64. The auger may include a shaft 72 and a helical fin 74 that winds around the shaft and projects laterally outward therefrom (see FIGS. 1-5, 7, and 8). Shaft 72 and fin 74 each may be flexible. This flexibility allows the auger to follow a curved entry site into bone and along the medullary cavity, and to operate efficiently in medullary cavities of different diameter. Auger 70 may be elastically deformable and oversized transversely relative to reamed diameter 66 of medullary cavity 54. Accordingly, fin 74 (and/or shaft 72) can be deformed by contact of fin 74 with the wall of the medullary cavity, to conform the auger locally to the medullary cavity (see FIGS. 2 and 3), particularly in a leading end region 76 of the auger forming the distal end thereof (see FIGS. 7 and 8). As a result, auger 70, and particularly fin 74, may wipe the wall of the medullary cavity as the auger is moved within the bone, helping to agitate and suspend osseous debris in fluid, which makes removal of osseous debris more efficient and/or improves the quality of the collected osseous debris for use in a bone graft. Fin 74 interchangeably may be described as a blade, which is substantially non-cutting.

Auger 70 may include a drive region 78 in proximal portion 58 of the harvesting device for engagement with a driver. The driver rotates the auger as a unit about its longitudinal axis 80 (see FIGS. 4-6). This rotation may be in a rotational direction that causes fin 74 to propel osseous debris 68 generally toward entry site 64, namely, clockwise (with respect to the user) for a fin having right-handed helicity, as in FIG. 1, or counter-clockwise for left-handed helicity. Drive region 78 may be formed as an axial extension and/or radial protrusion(s) (e.g., having one or more flats) firmly mounted to shaft 72 near or at the trailing end of the shaft. In other embodiments, drive region 78 may be formed by an exposed length of shaft 72 at which a driver, such as a K-wire driver, may engage and rotate the shaft.

The terms "proximal" and "distal" as used herein to describe portions, components, and features of harvesting device 50 and/or auger 70 generally denote relative proximity to drive region 78 and/or to a practitioner while used to harvest bone, with proximal being closer than distal to the drive region and/or the practitioner. The terms "trailing" and "leading" are used herein as respective synonyms for "proximal" and "distal." The terms "proximal" and "distal" as used herein to describe bones denote bone regions that are situated relatively closer to ("proximal") or farther from ("distal") the center of the body or the point of attachment.

Figures 4, 5, 6:
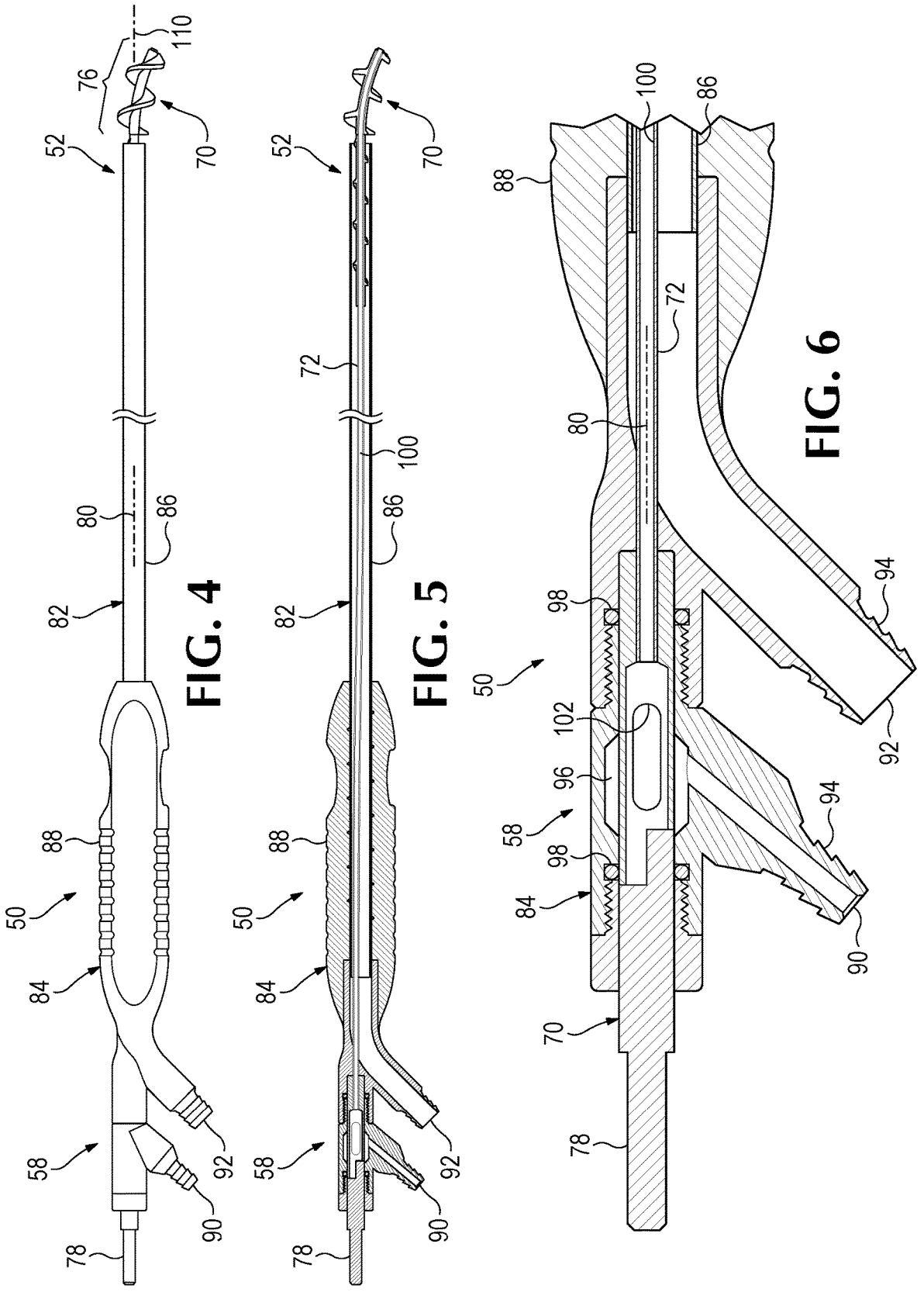
FIG. 4 is a side view of the bone harvesting device of FIG. 1 taken in the absence of bone and with the auger in a relaxed (undeformed) configuration.
FIG. 5 is a sectional view of the bone harvesting device of FIG. 4 taken at a central longitudinal plane of the device.
FIG. 6 is a fragmentary, magnified view of the sectioned bone harvesting device of FIG. 5, taken around a proximal portion of the device.

Bone harvesting device 50 may have a flexible shank 82 projecting distally from a housing 84 (see FIGS. 4-6). The shank may be formed by auger 70 alone or by the auger and a radially surrounding sleeve 86, among others. The diameter of shank 82, particularly where the shank includes sleeve 86, may be less than the diameter of entry site 64 (see FIG. 1).

Auger 70, housing 84, and sleeve 86 may have any suitable relationships to one another. An axial portion of auger 70 may be radially enclosed by housing 84, while the auger is permitted to rotate about longitudinal axis 80 with respect to housing 84 and/or sleeve 86. The housing may or may not be slidable axially along the shaft of the auger. Housing 84 may be firmly attached to sleeve 86. Accordingly, the axial position of the sleeve along the auger may be fixed or movable. A distal end of the sleeve may be configured to travel into the medullary cavity with the auger, or may remain substantially, such as completely, outside a bone as the auger is advanced into the bone (see Example 4).

Housing 84 is configured to remain outside bone during use of the bone harvesting device (see FIG. 1). The housing may include a graspable portion 88 sized to be grasped by a user's hand, to facilitate stabilizing, advancing, withdrawing, and/or orienting auger 70 (see FIGS. 4-6). The housing also or alternatively may form one or more ports for entry and/or exit of fluid during operation of the harvesting device. In the depicted embodiment, housing 84 has an inflow port 90 and an outflow port 92. Each of the ports may be formed by a hose nipple 94, which may be barbed (see FIG. 6).

Inflow port 90 can receive irrigation fluid from an external fluid source. The irrigation fluid can be driven into and/or through the harvesting device by negative pressure (e.g., vacuum applied via outflow port 92) and/or positive pressure applied upstream of inflow port 90. The inflow port can direct the fluid into a chamber 96 of housing 84 (see FIG. 6). Axial leakage from chamber 96 between auger 70 and housing 84 may be prevented by a pair of fluid-tight seals created by O-rings 98 positioned proximally and distally with respect to chamber 96. From chamber 96, the irrigation fluid may enter an axial channel 100 of auger 70 via a lateral opening 102 defined by the auger. Axial channel 100 may direct flow of the irrigation fluid, indicated by arrows at 104, to at least one exit site 106 defined by leading end region 76 of the auger outside sleeve 86 (see FIG. 8). Fluid leaves the auger within the medullary cavity at exit site 106. In the depicted embodiment, an axial exit site 106 is formed at the distal terminus of leading end region 76. In other embodiments, one or more radial exit sites may be formed radially along leading end region 76 (e.g., see Example 2).

Outflow port 92 can receive fluid (e.g., fluid carrying osseous debris 68) that is being pulled from housing 84 under negative pressure (i.e., suction (interchangeably called vacuum)) (see FIGS. 5 and 6). The fluid can enter sleeve 86 at its distal end, indicated by arrows at 107 (see FIG. 8). The fluid flows in a lumen 107a of sleeve 86 between the inside wall of the sleeve and the exterior of the auger before reaching housing 84. In some embodiments, the harvesting device can be operated without supplying irrigation fluid (e.g., see Examples 4 and 5) and/or without application of suction (e.g., see Example 5), and thus one or both ports 90, 92 may be eliminated.

Figures 7, 8:
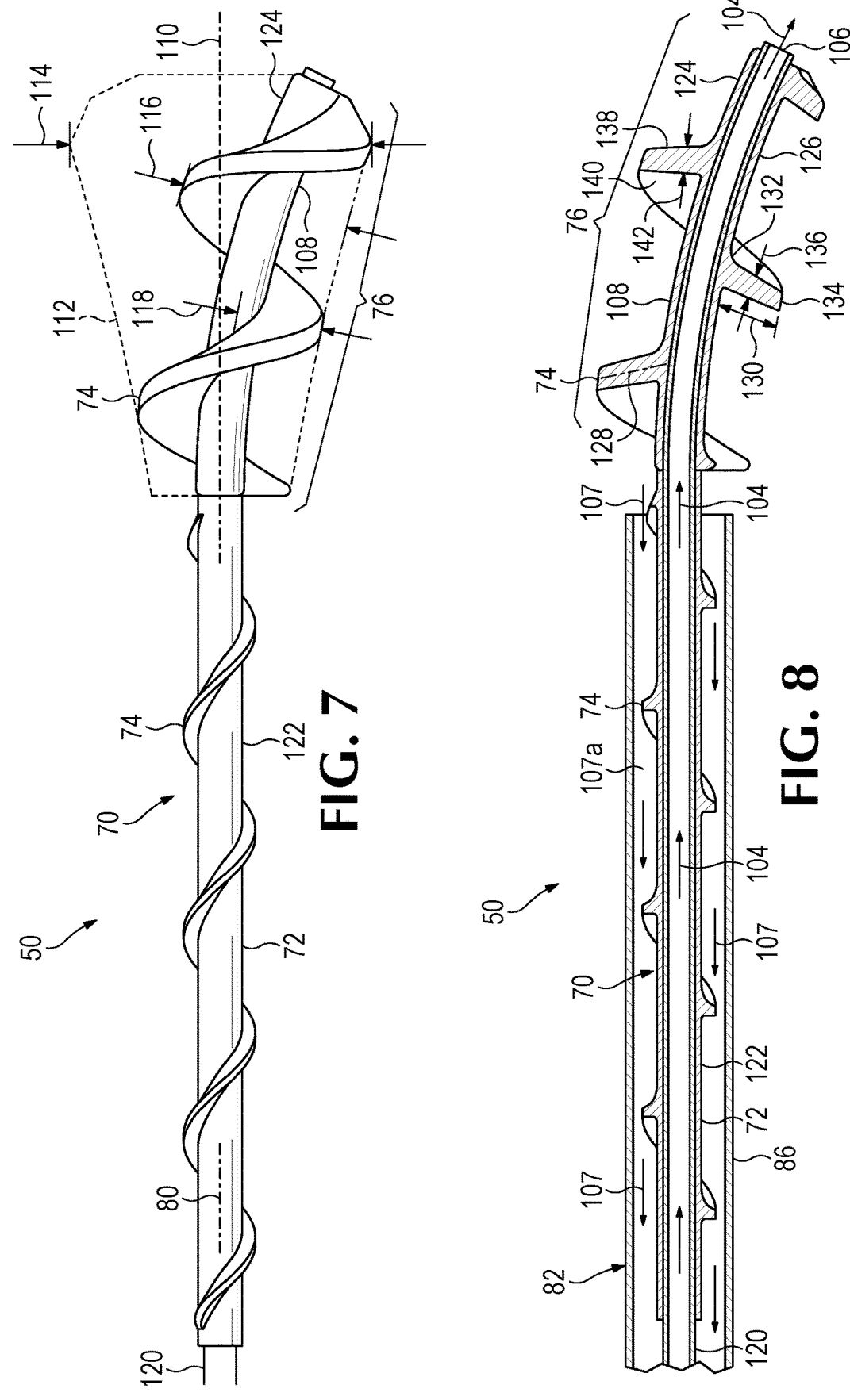
FIG. 7 is a fragmentary view of only the auger of the bone harvesting device of FIG. 4, taken with the auger in a relaxed (undeformed) configuration.
FIG. 8 is a fragmentary view of the sectioned bone harvesting device of Figure taken around the distal portion of the auger shown in FIG. 7, but in the presence of an encircling sleeve, with exemplary paths for fluid flow through the auger's shaft and the sleeve indicated by arrows.

FIG. 7 illustrates exemplary structural and dimensional aspects of auger 70, which is shown here in a relaxed (undeformed) configuration. Shaft 72 may have a non-linear leader 108 in leading end region 76, and at least an axial portion of helical fin may project from leader 108. More specifically, the shaft may be manufactured to be pre-bent, such that leader 108 bends away from a linear axis 110 that is coaxial with, or tangential to, longitudinal axis 80 of the shaft, at a position proximally adjacent leader 108. Accordingly, leader 108 may be arcuate as shown.

Auger 70 (and/or fin 74) defines an envelope of revolution 112 when rotated a full revolution about linear axis 110, and the envelope indicates the reach of helical fin 74 at each position along leading end region 76. (The rotation can be performed slowly and/or conceptually, such that the rotation does not substantially deform the auger.) The pre-bent configuration of leader 108 increases the size of envelope 112 relative to a leader that is linear. In other words, an envelope diameter 114 (interchangeably called a width) of envelope 112 is larger than an outer diameter 116 of helical fin 74, where outer diameter 116 is equal to twice the maximum radius 118 of auger in leading end region 76 measured from the local radial center of the auger. As a result, pre-bent leader 108, coupled with the elastic deformability of leader 108 and fin 74 in leading end region 76, allow the fin of the auger to remain in contact with the wall of the medullary cavity over a larger range of medullary cavity diameters (e.g., see FIGS. 2 and 3). Where the medullary cavity is narrower (as in FIG. 3), leader 108 may be deformed by contact with bone to have less curvature (i.e., a larger radius of curvature), such that the leader becomes straighter (i.e., more linear). In other embodiments, the outer diameter of the fin is equal to the diameter of the fin's envelope of revolution (i.e., if the leader of the shaft is linear).

Helical fin 74 may have any suitable characteristics (see FIG. 7). The fin may have a varying height. For example, the height may be larger, and optionally uniform, in leading end region 76, and smaller, and optionally uniform, proximal to leading end region 76. Alternatively, the fin may have a uniform height (e.g., see Example 3). The fin may be continuous or may be divided into two or more fin segments separated from one another by openings, such as slits (e.g., see Example 2). Fin 74 may wind around shaft 72 any suitable number of times, such as at least 1, 2, 3, 4, 5, 7, or 10 times, among others. The pitch of fin 74 may be constant or may vary along the fin. The auger may have only one fin 74 or two or more fins. The two or more fins may have no axial overlap, as FIG. 7, or may be axially overlapping.

FIGS. 7 and 8 show an exemplary construction for auger 70. The auger may include a rod 120 and one or more sheaths 122, 124 located on and covering at least an axial portion of the rod. Each sheath 122 or 124 may have a tubular base 126 that creates an outer layer of shaft 72, and a fin 74 winding around the tubular base (and optionally formed integrally with the base) (see FIG. 8). The sheath may be attached firmly to rod 120 with an adhesive, one or more fasteners, an interference fit, and/or the like. Rod 120 may be a tube, as depicted, or may be solid, among others.

Helical fin 74 may or may not project precisely radially from shaft 72. For example, fin 74 may project outward from shaft 72 along an axis of projection 128 having a proximal slant, as shown in FIG. 8, or a distal slant. The slant of the fin may create a preferential (proximal or distal) direction of deformation corresponding to the direction of slant, which can make the auger travel more easily along the medullary canal and/or improve the efficiency of wiping the wall of the medullary canal.

Fin 74 has a height 130 measured between a root 132 and a crest 134, in a direction orthogonal to the local longitudinal axis of shaft 72. A width 136 of the fin is measured between leading and trailing flanks 138, 140 of the fin. The fin may be substantially solid between the flanks. Height 130 may be greater than width 136, such as at least twice width 136, to provide sufficient flexibility and a desired amount of collapsibility of the fin.

Fin 74 may have an angle of taper 142 (or no taper) between flanks 138, 140. The angle of taper may be less than about 30, 20, 15, 10, or 5 degrees, among others. A smaller angle of taper can make the fin more flexible near the shaft, to encourage "folding" the fin in a proximal or distal direction toward the shaft, to accommodate a greater difference between the diameters of the fin and medullary cavity. A larger angle of taper can make the fin more rigid near the shaft, such that deformation occurs closer to the crest of the fin.

II. Methods of Obtaining Osseous Debris

This section describes exemplary methods of obtaining osseous debris. The method steps described in this section may be performed in any suitable order and combination, using any suitable bone harvesting device (and/or combination of device features) of the present disclosure. Further aspects of the methods are described elsewhere in the present disclosure, such as in Sections I and III.

A bone on which the method will be performed may be selected. Any suitable bone may be selected. The bone may, for example, be a long bone, such as a leg bone (e.g., a femur, tibia, or fibula) or an arm bone (e.g., a humerus, ulna or radius) of a subject, a pelvic bone (e.g., an illium), or a clavicle, among others. In preferred embodiments, the bone is a femur or tibia. In some embodiments, the bone selected may have a discontinuity (e.g., a fracture or cut) that will be fixed by installation of a fixation device, such as intramedullary nail or a plate, among others.

An entry site may be created in an exterior surface of the selected bone. If the bone is a long bone, the entry site may be formed near or at an anatomically proximal or distal end of the bone, either on the longitudinal axis of the bone or offset therefrom. The entry site may be formed with any suitable tool(s), such as an awl, a drill, or a combination thereof, among others. The entry site provides access to the medullary cavity of the bone.

The medullary cavity of the bone may be reamed. Reaming may be performed with at least one reaming device (a reamer) having a cutting head. The cutting head may be placed into the medullary cavity via the entry site formed in the bone. The cutting head may have a fixed diameter or an adjustable diameter. If the cutting head has a fixed diameter, the fixed diameter may be less than the diameter of the entry site. If the cutting head has an adjustable diameter, the cutting head may be placed into the medullary cavity via the entry site while the cutting head is in a contracted configuration having a diameter less than the diameter of the entry site. The cutting head then may be changed to an expanded configuration having a diameter greater than the diameter of the entry site after the cutting head is located inside the medullary cavity. At least a portion of the medullary cavity may be widened to a reamed diameter with the cutting head by removing osseous material from the wall of the medullary cavity, to generate osseous debris. The reamed diameter may be a single diameter, if the cutting head has a fixed diameter, or may be two or more different diameters, if an expandable cutting head is used. In some embodiments, reaming may be performed while supplying irrigation fluid to the medullary cavity. The osseous debris may represent cortical bone, medullary bone, or a combination thereof, and may be mixed with bone marrow, blood, and/or irrigation fluid, among others. In some embodiments, osseous debris may be generated with each cutting head of a succession of cutting heads having progressively increasing diameters. After reaming, the cutting head of the reamer(s) may be removed via the entry site.

An auger for removal of osseous debris may be selected. The auger may be part of a bone harvesting device also including any combination of a sleeve (interchangeably called an artificial tube), a housing, an inflow port and/or an outflow port, a collection vessel (optionally including a filter), a supply of irrigation fluid, and/or a source of suction, among others. The auger may have any suitable combination of features disclosed herein.

A distal portion of the auger, including a leading end region thereof, may be placed into the reamed medullary cavity via the entry site formed in the bone. The leading end region may have a maximum static diameter (when relaxed and stationary), and/or a maximum diameter of its envelope of revolution, that is greater than the diameter of the entry site and/or the reamed diameter. As a result, the leading end region, and particularly a helical fin therein, may be deformed as the leading end region is advanced through the entry site and/or enters the reamed portion of the medullary cavity. In some embodiments, the leading end region may be advanced past a reamed portion of the medullary cavity to an unreamed portion thereof.

The auger may be used to drive osseous debris toward the entry site. Osseous debris may be propelled by moving the auger axially (e.g., by pulling the auger progressively out of the bone and/or rotating the auger about its longitudinal axis. In some embodiments, the leading end region is pulled through a reamed portion of the medullary cavity while the auger is spinning. The auger may be rotated manually or with a motor at any suitable speed, such as faster than about 0.5, 1, 2, or 5 revolutions per second, among others. In exemplary embodiments, the auger is driven at about 750 revolutions per minute using a driver having a motor. Irrigation fluid may be supplied via the auger to the medullary cavity as the auger drives osseous debris. Travel of fluid and osseous debris out of the bone may be encouraged by application of suction at the exit site or inside the medullary cavity, among others.

Osseous debris that has passed through the exit site may be collected outside the bone. Collection may be performed with a collection vessel maintained at negative pressure, or with a tray disposed at ambient pressure, among others. The osseous debris may be filtered inside, or as it travels to, the collection vessel. Collected osseous debris may be implanted in the subject or another subject as a bone graft.

III. Examples

The following examples describe selected aspects and embodiments of the present disclosure related to bone harvesting methods and devices. These examples are included for illustration and are not intended to limit or define the entire scope of the present disclosure. The elements, steps, and features of the methods and devices described in this section may be combined with one another and with any of the elements, steps, and features described elsewhere in the present disclosure, in any suitable combination.

Example 1. Bone Harvesting Device with Sleeveless Auger

Figures 9, 10:
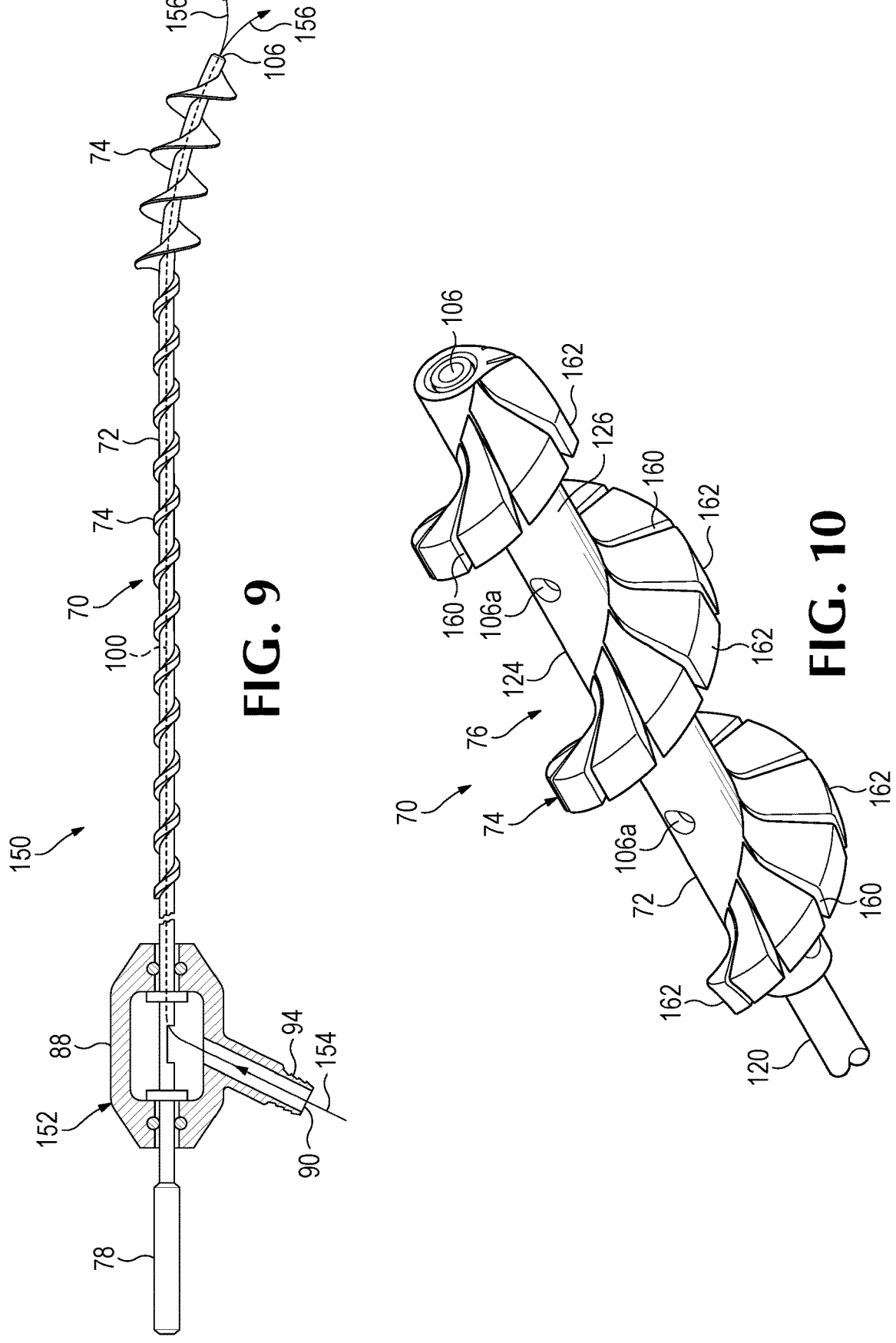
FIG. 9 is a partially sectional view of another exemplary bone harvesting device including an auger, wherein the distal portion of the auger that enters bone is sleeveless.
FIG. 10 is a fragmentary view of a leading end region of an exemplary auger having a helical fin composed of fin segments separated from one another by slits.

This example describes an exemplary bone harvesting device 150 utilizing a "sleeveless" auger 70 that is not radially surrounded by an artificial sleeve (interchangeably called an artificial tube) inside the medullary cavity to radially constrain osseous debris; see FIG. 9. Instead, the wall of the medullary cavity performs this function.

Harvesting device 150 is configured to remove osseous debris from a medullary cavity without the use of a sleeve to apply suction (compare with harvesting device 50 of FIGS. 1-8, particularly housing 84 and sleeve 86). Device 150 includes an auger 70 having any suitable combination of features described above in Section I, including a shaft 72, a helical fin 74, a drive region 78 for engagement with a driver, and an axial channel 100 for introducing irrigation fluid into the medullary cavity from an exit site 106. A housing 152 encircles a proximal portion of auger 70 that remains outside the bone, and provides a graspable portion 88 for manipulating the device. Housing 152 has an inflow port 90 formed by a hose nipple 94 and arranged in fluid communication with axial channel 100 of auger 70. Port 90 and channel 100 supply irrigation fluid to the medullary cavity in a manner similar to that of harvesting device 50, indicated by an inflow arrow at 154 and outflow arrows at 156. However, housing 152 does not have an outflow port for applying suction to aspirate fluid and osseous debris from the medullary cavity (also see Example 5 below).

Example 2. Auger with Segmented Helical Fin

This example describes an auger 70 having a helical fin 74 defining slits 160 that create a plurality of fin segments 162; see FIG. 10.

Auger 70 of this example may have any suitable combination of features described elsewhere herein, such as in Section I, and/or may be incorporated into any of the bone harvesting devices of the present disclosure. Fin 74 may define slits 160 arranged along the helical path of the fin. The slits may function to increase the flexibility of helical fin 74, which allows the fin to be formed by a sheath 124 of stronger, more rigid material. Each slit 160 may extend completely from the crest of fin 74 to shaft 72, or may extend only partway to shaft, such as traversing more than about 50%, 75%, or 90% of the fin's height and/or less than about 90%, 75%, or 50% of the fin's height. Helical fin 74 may have any suitable number of slits 160 per full turn of the fin, such as at least 2, 3, 4, or 5 slits.

One or more exit sites for irrigation fluid may be defined by a leading end region 76 of auger 70. An axial exit site 106 may be defined by a rod 120 structured as a tube. One or more radial exit sites 106a may be defined rod 120 and/or a tubular base 126 of sheath 124.

Example 3. Auger with Fin of Uniform Height

Figures 11, 12:
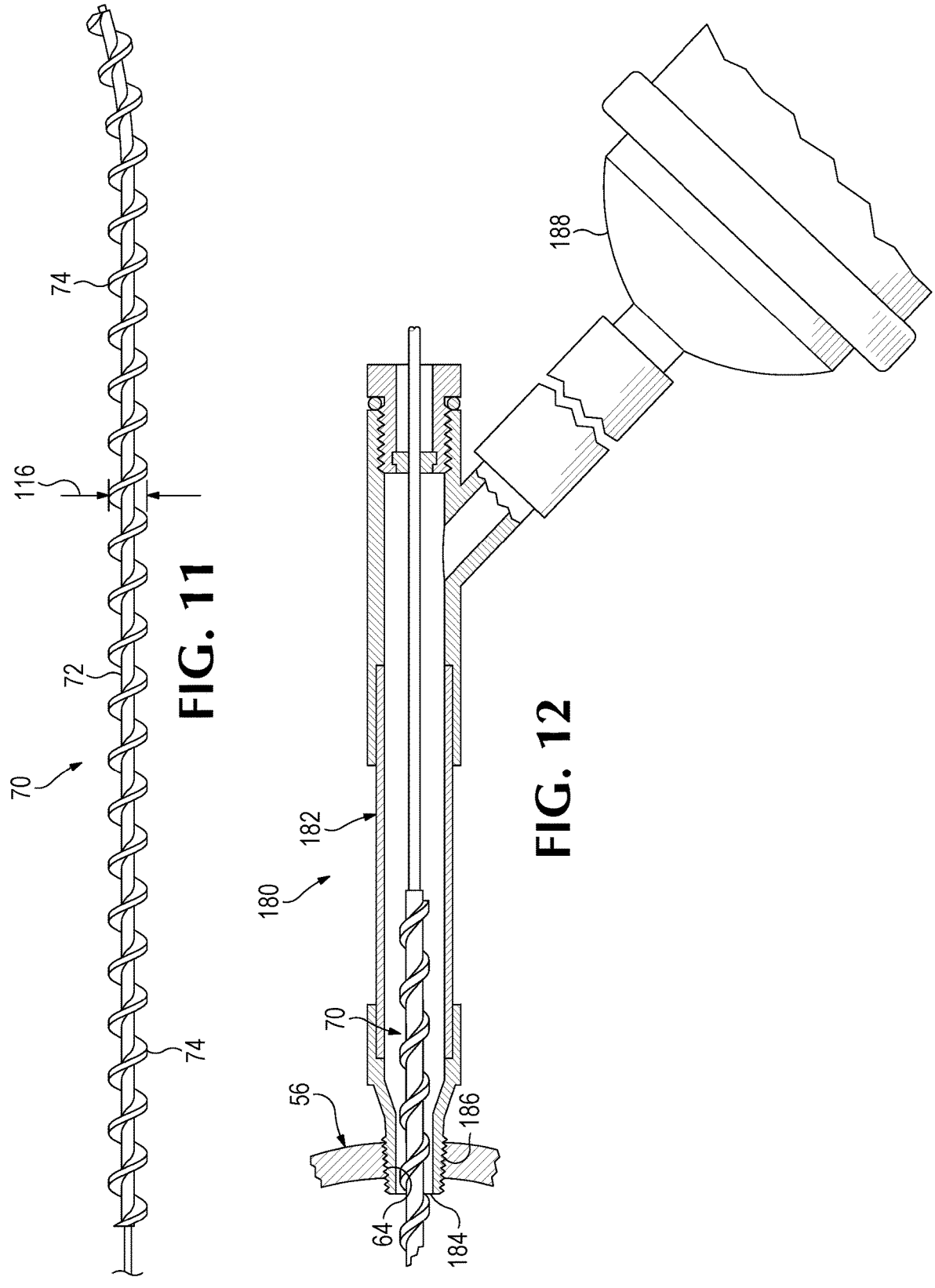
FIG. 11 is a fragmentary view of an exemplary auger having a helical fin of uniform height.
FIG. 12 is a fragmentary, proximal view of an exemplary bone harvesting device connected to a collection vessel, wherein the bone harvesting device includes an auger and a tube that is screwed into a bone and radially encloses only a proximal portion of the auger.

This example describes an exemplary auger 70 having a single helical fin of uniform height; see FIG. 11.

Auger 70 of this example may have any suitable combination of features described elsewhere herein, such as in Section I, and/or may be incorporated into any of the bone harvesting devices of the present disclosure. The auger may have a helical fin 74 with a constant outer diameter 116 along the length of the fin. Auger 70 may have a solid shaft 72, for use without irrigation fluid, or the shaft may be cannulated to permit delivery of irrigation fluid to the medullary cavity. Use of solid shaft 72 makes the auger stronger and less likely to break or kink.

Example 4. Bone Harvesting Device with Proximal Aspiration Tube

This example describes an exemplary bone harvesting device 180 having an auger 70 and a coaxial, proximal aspiration tube 182 that threads into distal femur 56 (or another bone or bone region); see FIG. 12.

Auger 70 may have any suitable combination of features disclosed elsewhere herein, such as Section I or other examples of Section III. The auger may be cannulated, to permit delivery of irrigation fluid, as described in Section I, or may be solid. Auger 70 extends through aspiration tube 182, and may have a drive region located proximal to the aspiration tube.

Aspiration tube 182 may have a distal tip 184 forming an external thread 186 for threaded engagement with entry site 64 in distal femur 56. This threaded engagement firmly attaches aspiration tube 182 to the bone.

The proximal end of tube 182 may be connected to a collection vessel having an outflow port at which suction is applied. Fluid that enters the collection vessel may pass through a filter that retains the osseous debris and separates it from the fluid.

In other embodiments, distal tip 184 may be replaced with a suction tip configured to apply suction at the surface of the bone without entering the bone. The suction tip may form a mouth that is wider than entry site 64. Accordingly, the suction tip may engage the outside surface of the bone around entry site 64 to form a seal when suction is applied. In some embodiments, the suction tip is formed by an elastomer.

Example 5. Tray for Collecting Osseous Debris

Figure 13:
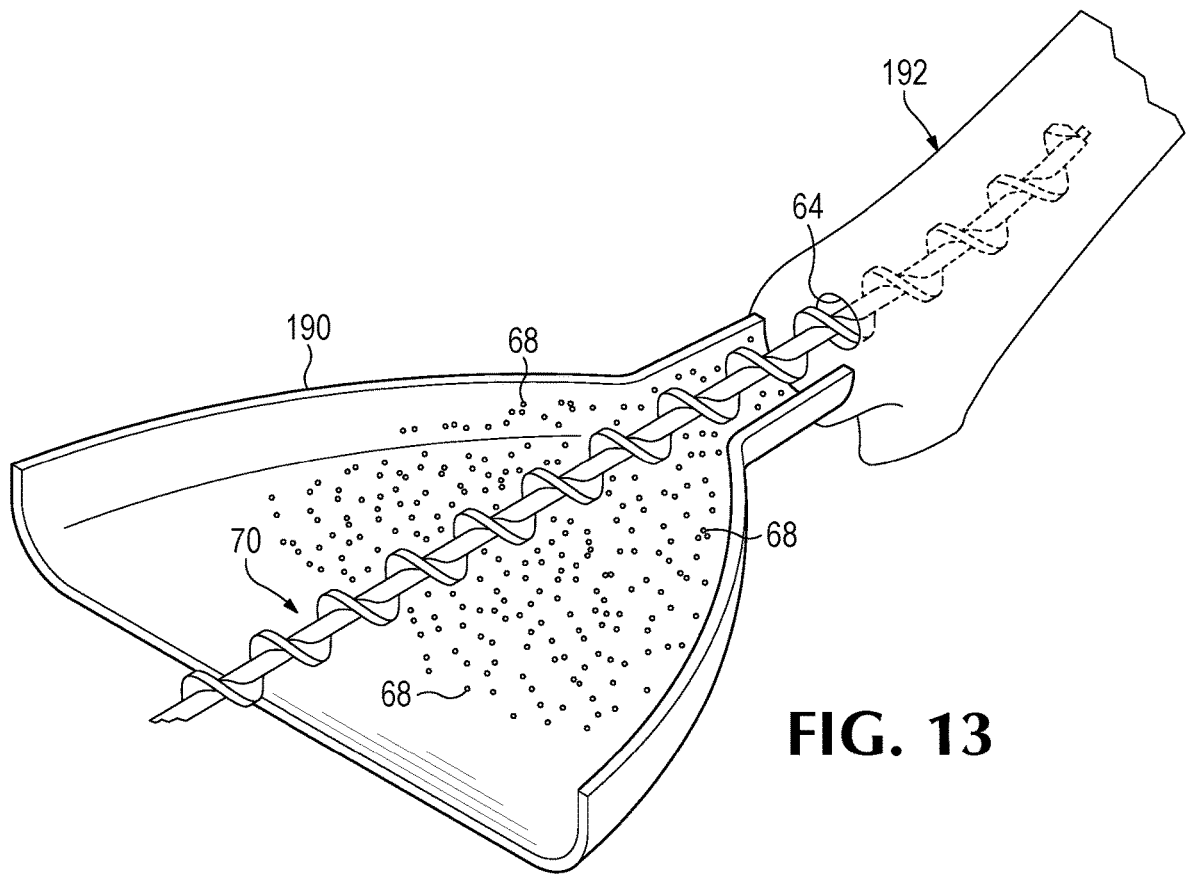
FIG. 13 is a view of osseous debris being harvested from the distal tibia via the medial malleolus using the auger of FIG. 11 and a collection tray to receive the osseous debris from the auger outside the tibia.

This example describes an exemplary tray 190 for collecting osseous debris 68 that has been transported out of a reamed bone 192 by a sleeveless auger 70; see FIG. 13 (also see FIGS. 9 and 11).

Bone 192 may, for example, be an anatomically distal portion of a tibia, as depicted, or any other suitable bone. An entry site 64 may formed in bone 192, and the bone may be reamed with a reamer to generated osseous debris 68. After removal of the reamer, auger 70 may be placed into the bone via entry site 64, and then may transport osseous debris 68 out of the bone via the entry site as the auger is rotated and/or withdrawn axially. The osseous debris may be collected in tray 190. In some embodiments, the osseous debris may fall off the auger into the tray without any assistance. In other embodiments, separation of the osseous debris from the auger may be assisted by application of fluid outside bone (e.g., a stream of fluid directed onto the auger outside bone) or use of separation tool (such as a spatula) attached to the tray, among others.

Example 6. Bone Harvesting Devices Equipped with a Reamer

Figures 14, 15:
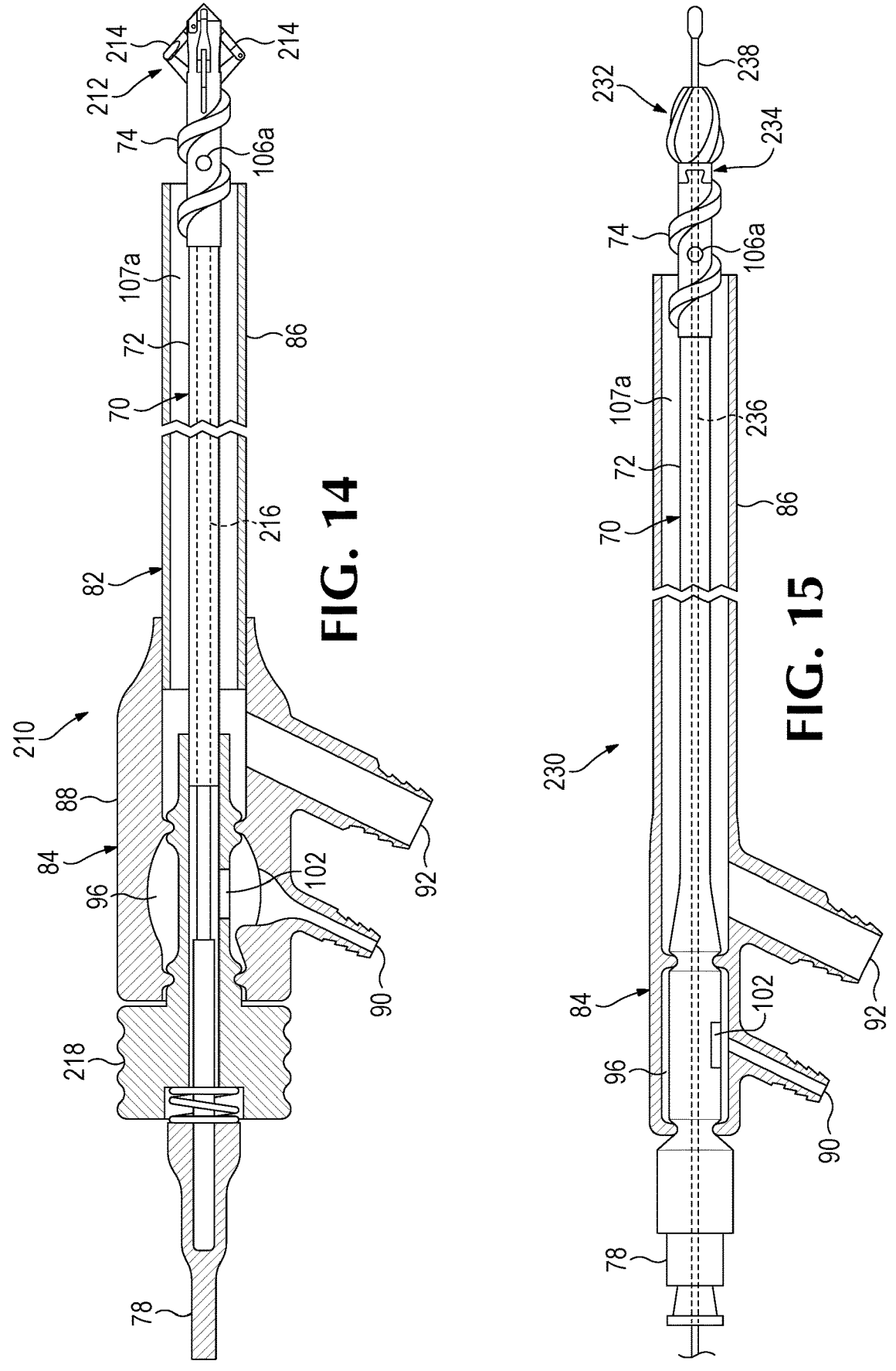
FIG. 14 is a partially sectional view of an exemplary bone harvesting device including a reamer with an expandable cutting head, and also including an auger located proximally with respect to the cutting head.
FIG. 15 is a partially sectional view of an exemplary bone harvesting device including a reamer with a replaceable cutting head, and also including an auger located proximally with respect to the cutting head.

This example describes exemplary bone harvesting devices also equipped with a cutting head to generate osseous debris by reaming; see FIGS. 14 and 15.

FIG. 14 shows a bone harvesting device 210 including an expandable cutting head 212 to ream a bone, and an auger 70 to facilitate transporting osseous debris out of the bone. The auger and cutting head rotate together as a unit when shaft 72 of the auger spins, which allows the device to ream bone and transport osseous debris at the same time.

Cutting head 212 may include a plurality of cutting members 214 that can be adjustably deployed to change the diameter of the cutting head. The deployment of the cutting members may be governed by an actuator 216, such as an axial rod inside shaft 72. The actuator is connected to a user interface 218, such as an adjustment knob. The user interface can be manipulated (e.g., rotated) to move actuator longitudinally, which changes the size of cutting head 212. Further aspects of an exemplary expandable cutting head that may be suitable are described in U.S. patent application Ser. No. 16/001,867, filed Jun. 6, 2018, which is incorporated herein by reference.

Bone harvesting device 210 and auger 70 thereof may have any suitable combination of features and elements described elsewhere herein. For example, device 210 may include a shank 82, a housing 84, a sleeve 86 radially surrounding an axial portion of auger 70 and forming a lumen 107a for uptake and travel of osseous debris. Housing 84 may form a graspable portion 88, an inflow port 90, an outflow port 92, and a chamber 96, as described above for bone harvesting device 50 in Section I. Auger 70 may include a shaft 72 having a proximal drive region 78 and defining an exit site 106a distally for fluid. The auger may have a helical fin 74 projecting from, and winding around, shaft 72.

Helical fin 74 may be located proximally of cutting head 212 and may extend around shaft 72 any suitable number of times inside and outside sleeve 86. For example, the fin may extend at least 1, 2, 3, or 5 times around shaft 72 inside sleeve 86 and/or outside the sleeve. The helical fin may have a constant height, or the height may vary (e.g., being larger outside relative to inside sleeve 86). In some embodiments, the maximum diameter of fin 74 distal to sleeve 86 may be greater than the outer diameter of the sleeve near the distal end thereof.

FIG. 15 shows a bone harvesting device 230 including a replaceable cutting head 232 to ream a bone, and an auger 70 to facilitate transporting osseous debris out of the bone. Auger 70 and cutting head 232 rotate together as a unit when shaft 72 of the auger spins, which allows the device to ream bone and transport osseous debris at the same time.

Device 230 may have any of the features and elements suitable for device 210 (see FIG. 14). Selected differences between the two devices are described here.

Cutting head 232 may be removably attached to shaft 72 of auger 70, such as at a coupling site 234. The cutting head can be replaced, as needed, with another cutting head of different size (e.g., to progressively increase the reamed diameter of the medullary cavity).

Device 230 may define an axial channel 236 extending completely through the device. The axial channel allows device 230 to be placed onto, and advanced along, a guide wire 238 that has been pre-installed in the bone.

Sleeve 86 may be formed integrally with housing 84, as depicted in FIG. 15. Alternatively, the sleeve may be formed separately (as in device 210).

Example 7. Selected Embodiments

This example describes selected embodiments of the present disclosure as a series of indexed paragraphs.

Paragraph 1. A method of obtaining osseous debris, the method comprising: (a) reaming at least a portion of a medullary cavity of a bone via an entry site extending into the bone, to generate osseous debris; (a) selecting an auger including a flexible, helical fin projecting from a shaft; (b) placing a leading end region of the auger into a reamed portion of the medullary cavity via the entry site; (c) driving at least a portion of the osseous debris toward the entry site using the helical fin of the auger; and (d) collecting, outside the bone, at least a portion of the osseous debris that has passed through the entry site; wherein placing and/or driving includes deforming the leading end region of the auger by contact between the helical fin and a wall of the medullary cavity, to conform the helical fin to the reamed portion of the medullary cavity.

Paragraph 2. The method of paragraph 1, wherein reaming includes reaming at least a portion of the medullary cavity to a reamed diameter, and wherein the auger has a relaxed configuration in which a diameter of the helical fin in the leading end region is greater than the reamed diameter.

Paragraph 3. The method of paragraph 1 or 2, wherein reaming includes reaming at least a portion of the medullary cavity to a reamed diameter, wherein the leading end region of the auger has a relaxed configuration defining an envelope of revolution having a diameter larger than the reamed diameter of the medullary cavity, and wherein placing and/or driving deforms the leading end region of the auger by contact between the helical fin and a wall of the reamed portion of the medullary cavity, to reduce the diameter of the envelope of revolution to match the reamed diameter of the medullary cavity.

Paragraph 4. The method of any of paragraphs 1 to 3, wherein the auger has a helical fin formed integrally with at least a portion of the shaft.

Paragraph 5. The method of paragraph 4, wherein the at least a portion of the shaft is tubular.

Paragraph 6. The method of any of paragraphs 1 to 5, wherein driving includes rotating the shaft about a longitudinal axis thereof.

Paragraph 7. The method of paragraph 6, wherein driving includes wiping the wall of the medullary cavity with the helical fin as the shaft is rotated.

Paragraph 8. The method of paragraph 6 or 7, wherein driving includes withdrawing an axial portion of the shaft from the medullary cavity as the shaft is rotating about the longitudinal axis.

Paragraph 9. The method of any of paragraphs 1 to 8, wherein auger has a relaxed configuration in which the shaft forms an arcuate leader in the leading end region, and wherein placing and/or driving includes deforming the leader radially by contact between the helical fin and the wall of the reamed portion of the medullary cavity.

Paragraph 10. The method of paragraph 9, wherein deforming the leader makes the arcuate leader less curved.

Paragraph 11. The method of any of paragraphs 1 to 10, wherein the auger is a non-cutting auger such that the steps of placing and driving do not substantially cut the bone.

Paragraph 12. The method of any of paragraphs 1 to 11, wherein the auger is associated with a sleeve that radially surrounds an axial portion of the shaft, wherein placing includes advancing a distal end of the sleeve along the medullary cavity, and wherein driving includes rotating the shaft about its longitudinal axis with respect to the sleeve.

Paragraph 13. The method of any of paragraphs 1 to 12, further comprising removing the leading end region of the auger from the medullary cavity, wherein no axial portion of the auger is radially surrounded by an artificial tube within the medullary cavity at any time during or between any steps of the method.

Paragraph 14. The method of any of paragraphs 1 to 13, wherein collecting includes applying suction to the bone at the entry site, to aspirate osseous debris into a tube located at least predominantly or exclusively outside the bone.

Paragraph 15. The method of any of paragraphs 1 to 14, wherein collecting includes collecting osseous debris in a tray outside the bone.

Paragraph 16. The method of paragraph 15, wherein collecting includes transferring osseous debris directly from the auger to the tray outside the bone.

Paragraph 17. The method of any of paragraphs 1 to 16, wherein reaming includes reaming the isthmus of the medullary cavity.

Paragraph 18. The method of any of paragraphs 1 to 17, wherein placing includes advancing the auger axially with respect to an artificial tube that radially surrounds an axial portion of the auger.

Paragraph 19. The method of paragraph 18, wherein driving includes moving the auger axially with respect to the artificial tube.

Paragraph 20. The method of paragraph 19, wherein collecting is performed at least in part as the auger is moved axially with respect to the artificial tube while a distal end of the artificial tube is at the entry site.

Paragraph 21. The method of any of paragraphs 18 to 20, further comprising disposing the artificial tube in threaded engagement with the bone at the entry site.

Paragraph 22. The method of any of paragraphs 18 to 20, wherein collecting includes aspirating osseous debris into the artificial tube outside the bone.

Paragraph 23. The method of any of paragraphs 1 to 22, wherein the leading end region of the auger has a diameter that is greater than a diameter of the entry site in the bone, when the leading end region is in a relaxed configuration, and wherein placing includes deforming the helical fin as it passes through the entry site of the bone.

Paragraph 24. The method of any of paragraphs 1 to 23, wherein the helical fin of the auger defines slits that form a plurality of fin segments arranged along a helical path.

Paragraph 25. The method of any of paragraphs 1 to 24, further comprising supplying irrigation fluid to the leading end region of the auger during driving via an axial channel defined by the shaft.

Paragraph 26. The method of any of paragraphs 1 to 25, wherein reaming is performed with one or more reamers, further comprising removing each of the one or more reamers from the bone via the entry site before placing.

Paragraph 27. A method of obtaining osseous debris, the method comprising: (a) creating an entry site extending into a bone; (b) placing a cutting head of a reamer into the medullary cavity of the bone via the entry site; (c) reaming at least a portion of the medullary cavity to a reamed diameter with the cutting head to generate osseous debris; (d) removing the cutting head from the medullary cavity via the entry site; (e) selecting an auger including a flexible, helical fin projecting from a shaft, wherein a leading end region of the auger has a diameter greater than the reamed diameter; (f) placing at least the leading end region of the auger into the medullary cavity via the entry site; (g) driving osseous debris toward the entry site as the helical fin is deformed by contact with a wall of a reamed portion of the medullary cavity, such that the diameter of the leading end region of the auger matches the reamed diameter of the medullary cavity; and (h) collecting osseous debris that has passed through the entry site.

Paragraph 28. The method of paragraph 27, wherein the step of driving osseous debris includes spinning the auger about a longitudinal axis of the shaft.

Paragraph 29. A device for removing osseous debris from a pre-reamed medullary cavity of a bone, the device comprising: an auger having a leading end region configured to be placed into the medullary cavity, the auger including a flexible, helical fin projecting from a shaft.

Paragraph 30. The device of paragraph 29, wherein the helical fin and at least a portion of the shaft are formed integrally with one another.

Paragraph 31. The device of paragraph 30, wherein the at least a portion of the shaft is tubular.

Paragraph 32. The device of any of paragraphs 29 to 31, wherein the shaft includes a rod, and wherein the helical fin is provided by a sheath that is disposed on and firmly attached to an axial portion of the rod.

Paragraph 33. The device of paragraph 32, wherein the rod is solid.

Paragraph 34. The device of paragraph 32, wherein the rod is hollow.

Paragraph 35. The device of any of paragraphs 32 to 34, wherein the sheath is a polymer sheath, and wherein the rod is a metal rod.

Paragraph 36. The device of any of paragraphs 29 to 35, wherein the helical fin projects at an acute angle from the shaft in the leading end region of the auger.

Paragraph 37. The device of paragraph 36, wherein the acute angle is less than degrees.

Paragraph 38. The device of any of paragraphs 29 to 37, wherein the helical fin has a proximal or distal slant in the leading end region of the auger.

Paragraph 39. The device of paragraph 38, wherein the helical fin is configured to preferentially deform in a direction of the slant, relative to an opposite direction.

Paragraph 40. The device of any of paragraphs 29 to 39, wherein the helical fin of the auger defines a plurality of slits forming a plurality of fin segments arranged along a helical path.

Paragraph 41. The device of any of paragraphs 29 to 40, wherein the helical fin has a height measured between a root and a crest of the helical fin, and wherein the height has an average in the leading end region of the auger that is greater than one-half an average outer diameter of the shaft in the leading end region of the auger.

Paragraph 42. The device of any of paragraphs 29 to 41, wherein the average of the height is greater than the average outer diameter of the shaft.

Paragraph 43. The device of any of paragraphs 29 to 42, wherein the helical fin projects from an arcuate leader of the shaft in the leading end region of the auger, when the auger is in a relaxed configuration.

Paragraph 44. The device of any of paragraphs 29 to 43, wherein the helical fin has an average height and an average thickness in the leading end region of the auger, wherein the average thickness is measured between a leading flank and a trailing flank of the helical fin, and wherein the average height is greater than the average thickness.

Paragraph 45. The device of paragraph 44, wherein the average height is at least twice the average thickness.

Paragraph 46. The device of any of paragraphs 29 to 45, wherein the helical fin in the leading end region of the auger has an average angle of radial taper of less than twenty degrees.

Paragraph 47. The device of any of paragraphs 29 to 46, wherein the helical fin in the leading end region of the auger has a pitch that is more than three times a maximum thickness of the helical fin measured between a leading flank and a trailing flank of the helical fin in the leading end region.

Paragraph 48. The device of any of paragraphs 29 to 47, wherein the helical fin has a leading flank and a trailing flank, and wherein the helical fin is substantially solid between the leading and trailing flanks.

Paragraph 49. The device of any of paragraphs 29 to 48, wherein at least an axial portion of the helical fin and a portion of the shaft are formed integrally with one another, wherein the portion of the shaft has an outer surface, and wherein the axial portion of the helical fin projects from the outer surface of the portion of the shaft.

Paragraph 50. The device of paragraph 49, wherein the portion of the shaft includes a tube.

Paragraph 51. The device of paragraph 49 or 50, wherein the outer surface is cylindrical.

Paragraph 52. The device of any of paragraphs 49 to 51, wherein the tube forms an outer portion of the shaft, and wherein the tube encircles an inner portion of the shaft.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated. Finally, the present disclosure incorporates material by reference. If any ambiguity or conflict in the meaning of a term results from this incorporation by reference, the literal contents of the application govern construction of the term.

We claim:

1. A bone harvesting device comprising:
a housing; and
an auger including a flexible shaft and a flexible helical fin extending from the flexible shaft, the flexible shaft having a distal region opposite a proximal region,
wherein the proximal region of the auger includes a drive region configured to engage with a drive instrument for rotating the auger and the distal region of the auger includes the flexible helical fin,
wherein an outer diameter of the flexible helical fin in a leading end region of the flexible shaft is greater than an outer diameter of the flexible helical fin in a region of the flexible shaft proximally adjacent the leading end region,
wherein each the flexible shaft and the flexible helical fin are elastically deformable, and
wherein the housing encloses a portion of the auger.

2. The bone harvesting device of claim 1, wherein the outer diameter of the flexible helical fin in the leading end region is uniform.

3. The bone harvesting device of claim 1, wherein the outer diameter of the flexible helical fin in the region of the flexible shaft proximally adjacent the leading end region is uniform.

4. The bone harvesting device of claim 1, wherein the flexible helical fin comprises a proximal or distal slant in the leading end region of the flexible shaft.

5. The bone harvesting device of 4, wherein the helical fin is configured to preferentially deform in a direction of the slant, relative to an opposite direction.

6. The bone harvesting device of claim 1, wherein the flexible helical fin extends from the flexible shaft along an axis of projection, wherein the axis of projection of at least a portion of the flexible helical fin forms an angle with the flexible shaft of less than ninety degrees.

7. The bone harvesting device of claim 1, wherein at least a portion of the flexible helical fin is tapered such that a width of the flexible helical fin is greater at the flexible shaft than at a crest of the flexible helical fin.

8. The bone harvesting device of claim 1, wherein the flexible helical fin and at least a portion of the flexible shaft are formed integrally with one another.

9. The bone harvesting device of claim 1, wherein at least a portion of the shaft is tubular.

10. The bone harvesting device of claim 1, wherein the flexible shaft includes a flexible sheath surrounding a flexible rod, and wherein the flexible helical fin extends from the flexible sheath.

11. The bone harvesting device of claim 10, wherein the flexible rod is hollow.

12. The bone harvesting device of claim 11, wherein the flexible rod is solid.

13. The bone harvesting device of claim 1, wherein the housing comprises on or more ports for entry and/or exit of fluid.

14. A bone harvesting device comprising:
an auger including a flexible shaft and a flexible helical fin extending from the flexible shaft, the flexible shaft having a distal region opposite a proximal region,
wherein an outer diameter of the flexible helical fin in a leading end region of the flexible shaft is greater than an outer diameter of the flexible helical fin in a region of the flexible shaft proximally adjacent the leading end region, and
wherein each the flexible shaft and the flexible helical fin are elastically deformable.

15. The bone harvesting device of claim 14, wherein the outer diameter of the flexible helical fin in the leading end region is uniform.

16. The bone harvesting device of claim 15, wherein the flexible helical fin comprises a proximal or distal slant in the leading end region of the flexible shaft, wherein the helical fin is configured to preferentially deform in a direction of the slant, relative to an opposite direction.

17. The bone harvesting device of claim 14, wherein the outer diameter of the flexible helical fin in the region of the flexible shaft proximally adjacent the leading end region is uniform.

18. The bone harvesting device of claim 14, wherein the flexible helical fin and at least a portion of the flexible shaft are formed integrally with one another.

19. The bone harvesting device of claim 14, wherein the flexible shaft includes a flexible sheath surrounding a flexible rod, and wherein the flexible helical fin extends from the flexible sheath.

* * * * *